(12) United States Patent
Monnier et al.

(10) Patent No.: US 6,325,801 B1
(45) Date of Patent: Dec. 4, 2001

(54) INSTRUMENT FOR SEVERING TISSUE WITH HF CURRENT

(75) Inventors: Philippe Monnier, Pully; Pierre Grosjean, Villars-Tiercelin, both of (CH)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/455,734

(22) Filed: Dec. 4, 1999

(51) Int. Cl.⁷ ..................................................... A61B 18/18
(52) U.S. Cl. .................................. 606/46; 606/41; 606/45
(58) Field of Search .................................. 606/41, 45, 46, 606/48, 50; 600/105, 562, 564, 565

(56) References Cited

U.S. PATENT DOCUMENTS

| | | |
|---|---|---|
| 3,835,842 * | 9/1974 | Iglesias .................. 600/105 |
| 5,275,609 | 1/1994 | Pingleton et al. . |
| 5,423,813 | 6/1995 | Kaiser et al. . |
| 5,423,830 | 6/1995 | Schneebaum et al. . |
| 5,527,332 | 6/1996 | Clement . |
| 5,913,857 * | 6/1999 | Ritchart et al. ............... 606/45 |
| 6,019,733 * | 2/2000 | Farascioni .................. 600/564 |
| 6,030,383 * | 2/2000 | Benderev .................. 606/45 |
| 6,077,230 * | 6/2000 | Gregoire et al. ............... 600/566 |
| 6,142,955 * | 11/2000 | Farascioni et al. .................. 600/562 |
| 6,197,025 * | 3/2001 | Grossi et al. ............... 606/46 |

FOREIGN PATENT DOCUMENTS

| | | |
|---|---|---|
| 44 29 478 C1 | 3/1996 | (DE) . |
| 195 01 258 A1 | 7/1996 | (DE) . |

\* cited by examiner

*Primary Examiner*—Michael Peffley
(74) *Attorney, Agent, or Firm*—St. Onge Steward Johnston & Reens LLC

(57) ABSTRACT

What is described here is an instrument for severing tissue, comprising an elongate instrument body adapted to be introduced into the human or animal body, an HF electrode array provided on the instrument body, to which an HF current may be applied, and an aspirator or vacuum means. In accordance with the invention the instrument body is provided with an aspirator element at a region coming into contact with the tissue, to which aspirator element a negative pressure is applied by means of the suction means in such a way that tissue is aspirated against the instrument body, and that at least one part of the electrode array is adapted for movement in parallel with the aspirator element such that the tissue aspirated against the instrument body will be removed between the aspirator element and the moved part of the electrode array.

23 Claims, 2 Drawing Sheets

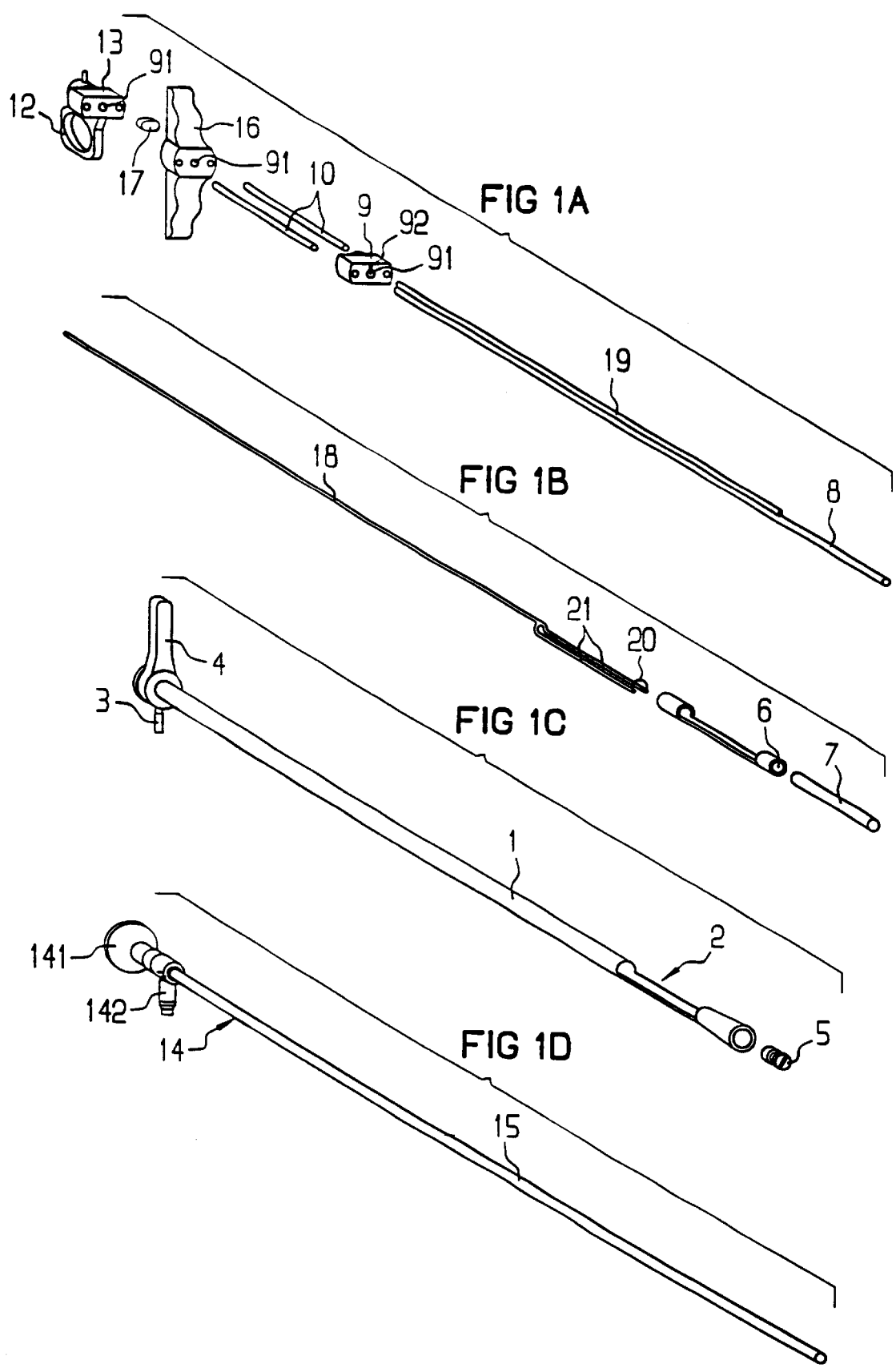

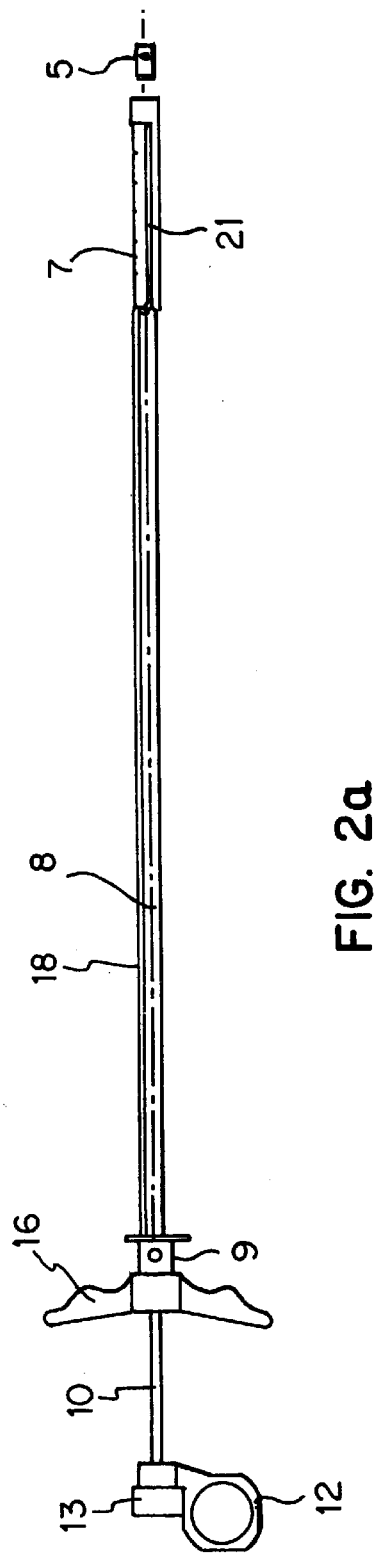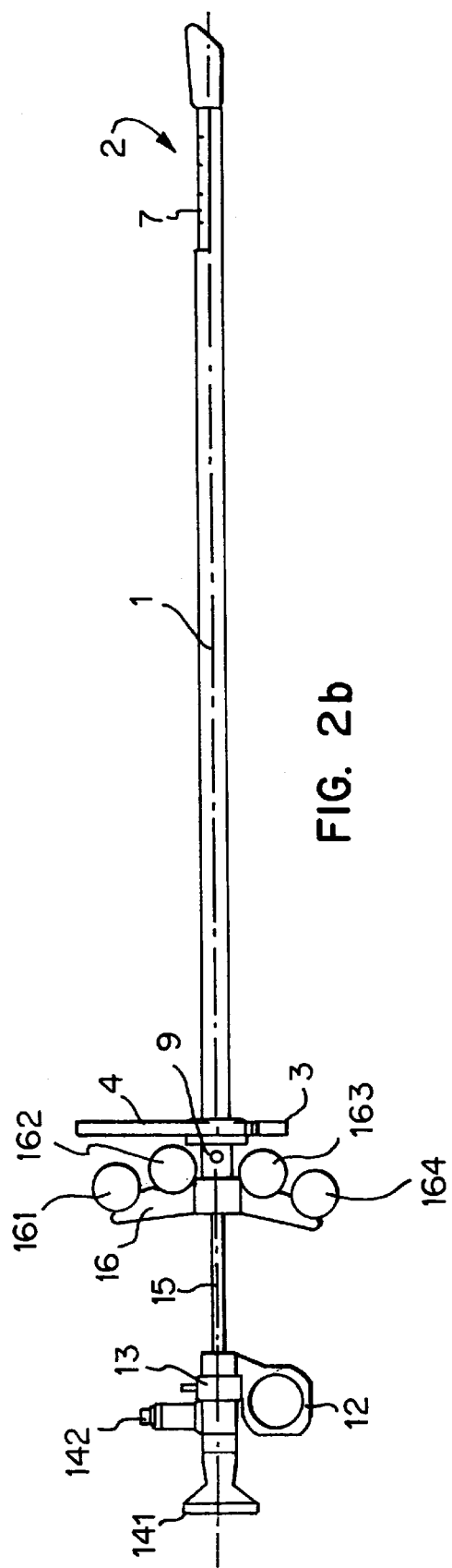
FIG. 2a
FIG. 2b

INSTRUMENT FOR SEVERING TISSUE WITH HF CURRENT

FIELD OF THE INVENTION

The present invention relates to an instrument of cutting tissue.

PRIOR ART

An instrument for cutting tissue is known from the U.S. Pat. No. 5,423,830. That instrument, which is intended, express is verbis, for removal of adenoids, includes an HF coil which is pushed over the adenoid. Then the adenoid is aspirated into a suction cup and the base of the adenoid is then severed with the coil.

The known instrument is hence not appropriate for severing tissue, specifically mucous membrane material, in the form of strips, as it is necessary, for instance, in certain treatment operations on elongate organs, e.g. the oesophagus.

An instrument of a slightly varied type is known from the German Patent DE 44 29 478 C1. That instrument includes, in addition to a cutting means operated with high frequency, an extractor tube through which the severed tissue fragments may be aspirated. This instrument, too, is not suitable for severing tissue such as mucous membrane material in strips.

BRIEF DESCRIPTION OF THE INVENTION

The present invention is based on the problem of providing an instrument for severing tissue with HF current, which is suitable for severing the tissue in the form of strips having a specified thickness.

In accordance with the invention the body of the instrument comprises an aspirator element in the region coming into contact with the tissue, to which element a negative pressure is applied by means of the suction means such as a pump in a way that tissue is aspirated to the instrument body, particularly in the region of the aspirator element. In distinction from prior art, it is intended here that the tissue is not aspirated into the instrument body but should merely "adhere" to the instrument body under the suction effect. For severing strip-shaped tissue fragments having a substantially constant thickness at least one part of the electrode system is moved in parallel with the aspirator element in such a way that the tissue aspirated to the instrument body is removed between the aspirator element and the moving part of the electrode system.

Even though the aspirator element may also be provided in the distal face of the instrument, an improvement is preferred whereby the aspirator element has a preferably cylindrical outside surface in which a hole array with at least one hole is provided or which is of a permeable design. The negative pressure is then applied to the cylindrical outside surface from inside. If a hole array is used it is preferable that this array includes a plurality of holes of a comparatively small diameter because in such a case a high aspiration effect is achieved without the potential risk of tissue being "sucked into" the instrument body.

The HF electrode system in the instrument may be both a monopolar electrode, with the backplate electrode being mounted on the body at a distance, and a bipolar electrode array.

When the instrument comprises a monopolar electrode the latter is formed by the mobile part of the electrode array whilst the other electrode is (preferably) constituted by the cylindrical outside surface.

Independently of the use of a monopolar or bipolar electrode array it is preferable that the mobile part of the electrode array presents the shape of an HF cutting coil known per se. The precise form of the coil or loop is adapted to the outside contour of the aspirator element.

The coil is disposed at a predetermined spacing along a direction normal on the surface of the aspirator element, which space determines the thickness of the severed tissue strip. For tissue cutting the coil is preferably moved from the distal end towards the proximal end because the power transmission is easier to "dose" when working in "traction mode" than this would be the case when working in "pressing mode."

A particular embodiment of the inventive instrument in which substantially unvaried or only slightly modified "modular elements" of known endoscope and HF resection systems may be used: in this design the instrument body comprises a first hollow shaft which corresponds essentially to known endoscope shafts. This hollow shaft is so modified that it carries the aspirator element laterally. On its proximal end a connector known per se is provided for the suction means, such as a suction pump which may be a glass filter pump, a reciprocating pump, a rotary pump or the like.

A particularly low-cost production and moreover the suitability for easy sterilization and cleaning of the inventive instrument are achieved by the provision that the lateral hole array or the permeable region, is provided in the external wall of a hollow body which is inserted into a recess in the first shaft. The hollow body may consist of an electrically insulating material, e.g. a ceramic or glass material, quartz or a synthetic material, especially when the electrode array is a monopolar electrode.

In such a case it is preferable that the hollow body is transparent because in such a case an observation is possible by means of an endoscope inserted into the first shaft through the transparent hollow body. When comparatively wide holes are used it is possible, of course, to produce the hollow body also from a non-transparent material and to provide for observation through the holes.

Instead of an optical lateral viewing endoscopic system also an optical retro-system may be used which projects beyond the distal end of the first shaft. In the event that the optical endoscopic system is guided through the duct of the first shaft, through which the material is also withdrawn, a seal must possibly be provided on the distal end.

In any case, it is preferable that the optical endoscopic system is suitable for axial displacement.

In further embodiments, the hollow body is inserted into a supporting element together with which it is inserted into the first shaft, and the supporting element is fastened in the first shaft by means of a screw introduced into the distal face of the first shaft, to improve the suitability of the instrument for cleaning and sterilizing.

To permit a simple displacement of the mobile electrode with a small structure and, particularly, a low lumen requirement, a feeder line for the current supply of the electrode array is arranged outside the axis in the first shaft and configured as a connecting or traction rod; furthermore, a handle is attached on the proximal end of the traction rod, and a manipulator is disposed on the first shaft.

BRIEF DESCRIPTION OF THE DRAWING

The invention will be described in the following in more details by the example of an embodiment, with reference to the drawing in which:

FIGS. 1*a* to *d* show an "exploded view," and

FIGS. 2*a* and *b* are lateral views of the instrument shown in FIG. 1, in different stages of assembly.

DESCRIPTION OF A PREFERRED EMBODIMENT

First of all, the fundamental structure of the inventive instrument will be explained with reference to FIGS. 1*a* to 1*d*, which are, by the way, explicitly referred to with respect to the configuration of all—possibly also essential—details which are not mentioned express is verbis in the description.

The inventive instrument for severing tissue, and specifically in a cavity of a human or animal body, comprises a first hollow shaft 1 (FIG. 1*c*) which includes a lateral recess 2 in its cylindrical peripheral or outside surface in the region of its distal end. On the proximal end of the shaft 1 a fitting 3 is provided for connecting a suction means such as a suction pump, and a manipulator or handle 4. In the face of the distal end of the hollow shaft a screw 5 is provided which has a function that will be explained in the following.

A supporting element 6 (FIG. 1*b*) is inserted into the first hollow shaft 1 for receiving a hollow body 7 in such a way that one part of the cylindrical outer surface of the hollow body will be "exposed" on account of the lateral recess 2 of the hollow shaft 1. The hollow body 7 comprises a plurality of holes in its cylindrical outside surface, to which holes a negative pressure may be applied by means of the suction pump which is not illustrated here and which is connected to the fitting 3.

In the illustrated embodiment the supporting element 6 is screwed to the shaft 1 by means of the screw 5 through the distal face of the shaft.

A second hollow shaft 8 (FIG. 1*a*) is inserted into the first hollow shaft 1 and has a distal face which adjoins that face of the supporting element 6 which faces the proximal end. In the illustrated embodiment the second hollow shaft 8 and the supporting element 6 are not connected to each other, but it is also possible, of course, to connect the supporting element to the second hollow shaft 8 as an alternative of screwing the supporting element 6 through the distal face of the first hollow shaft. A connecting block 9 is provided on the proximal end of the second hollow shaft 8, which has a through bore 91 aligned with the central duct of the hollow shaft 8 and which includes another through bore 92 having a function which will be explained below.

Two guiding rods 10 are provided on the proximal side of the connecting block 9, with the other ends thereof being supported in another block 11. On the further block 11 a first handle 12—in the illustrated embodiment a thumb ring—and a coupler 13 for instruments are provided, such as a bayonet coupler known per se. The further block 11 equally includes a through bore 91 which is aligned with the central duct of the second shaft 8.

Consequently a conventional endoscope 14 (FIG. 1*d*) with an eyepiece 141 and a light guide fitting 142 can be inserted into the coupler 13 in such a way that the shaft 15 of the endoscope 14 passes through the through bores 91 of the blocks 9 and 13 as well as through the second hollow shaft 8 and—at least partly—through the elements 6 and 7.

A second handle 16 is supported for displacement on the two guiding rods 10; this second handle is provided with stops for the index finger 161, the middle finger 162, the ring finger 163 and the small finger 164—as is shown in FIG. 2*b*.

On the proximal side of the second handle 16 a fitting 17 is provided for connecting one pole of a surgical HF instrument, which is not illustrated here, which fitting is connected to the rod 18 through the bore 92. In the illustrated embodiment, the other pole of this surgical HF instrument is connected to a neutral electrode, which is not shown and which is applied, in a manner known per se, on the body surface of the treated human or animal body.

A rod-shaped part 18 (FIG. 1*b*), which is guided in a guide 19 (FIG. 1*a*) on the surface of the second hollow shaft 8 is connected to the fitting 17 via the handle 16. Via the distal end of the part 18 an HF coil 20 is connected via connector 21. The rod-shaped part 18 serves to supply the HF coil 20 with current and as a transmission element for transmitting tensile or compressive force.

FIG. 2*a* shows the embodiment of an inventive instrument wherein the first hollow shaft 1 (external shaft) has been omitted so that the supporting element 6 with the hollow body 7, the distally disposed screw 5 and the second hollow shaft 8 with the HF coil 20 are visible. Here the elements identical with those of FIG. 1 are identified by the same numerals.

FIG. 2*b* illustrates the embodiment with the first hollow shaft 1 (external shaft) in place, whilst additionally the endoscope 14 is inserted into the second hollow shaft 8. Moreover, the index finger 161, the middle finger 162, the ring finger 163 and the small finger 164 are illustrated in an abstracted form to bear against the stops on the second handle 16.

The inventive instrument for severing tissue by means of HF current operates as follows:

In a first step, the instrument is introduced into the cavity of the human body and contacted with the intracorporeal tissue. In a "non-endoscopic" application the instrument is, of course, contacted only with the "superficial" tissue to be cut. The HF coil 20 is in its distal terminal position.

Subsequently, the suction means, such as a pump, is turned on so that a negative pressure is applied to the hollow body 7 which serves as aspirator element. As a result of this negative pressure the tissue to be cut is "aspirated" against the hollow body so as to "adhere" to the latter.

Now the surgical HF instrument is turned on so that with a monopolar electrode array a current will flow between the cutting coil 20 and a neutral electrode. When a bipolar electrode array is used the current flows correspondingly between the cutting oil 20 and the instrument body, e.g. the hollow body 7.

After activation of the HF current the HF cutting coil 20 is moved in parallel with the surface of the hollow body 7 by retraction of the handle 16. This action causes a removal of the tissue aspirated against the instrument body between the aspirator element and the moved part of the electrode array, i.e. the coil 20.

The invention has been described in the foregoing with reference to an embodiment without any limitation of the general inventive idea within the scope of which the most different modifications are possible, of course.

What is claimed is:

1. Instrument for severing tissue, comprising
    an elongate instrument body adapted to be introduced into the human or animal body,
    an HF electrode array to which an HF current may be applied and which is adapted to be displaced in a direction parallel to a longitudinal axis of the instrument body, and
    a pump applying a negative pressure to an aspirator element, characterized in that said aspirator element is provided laterally in an outside surface of said instrument body and in that said electrode array comprises a coil which is disposed laterally on the instrument body at a defined spacing therefrom and which has a shape adapted to a cross-sectional contour of the outside surface so that tissue aspirated against the aspirator element will be removed in layers by the displacement of said coil in a direction along the longitudinal axis of the instrument.

2. Instrument according to claim 1, characterized in that the outer surface has a cylindrical configuration, and that at least one hole in the outer surface constitutes said aspirator element.

3. Instrument according to claim 2, characterized in that a plurality of holes is provided.

4. Instrument according to claim 2, characterized in that said instrument body presents a first hollow shaft which carries said aspirator element on one side and which comprises a fitting for connection of the pump on its proximal end.

5. Instrument according to claim 4, characterized in that the aspirator element is provided in the external wall of a hollow body which is inserted into a recess in said first shaft.

6. Instrument according to claim 5, characterized in that said hollow body consists of an electrically insulating material.

7. Instrument according to claim 6, characterized in that said electrically insulating material is selected from the group consisting of a ceramic material, a glass material, $SiO_2$, a synthetic material, and combinations of these.

8. Instrument according to claim 7, characterized in that said hollow body is transparent.

9. Instrument according to claim 6, characterized in that said hollow body is inserted into a supporting element together with which it is inserted into said first shaft.

10. Instrument according to claim 9, characterized in that said supporting element is fastened in said first shaft by means of a screw introduced into a distal face of said first shaft.

11. Instrument according to claim 5, characterized in that a laterally viewing optical endoscopic system is provided with a field of view oriented through said transparent hollow body.

12. Instrument according to claim 8, characterized in that a feeder line for current for said electrode array is arranged outside the axis in said first shaft and configured as a connecting rod.

13. Instrument according to claim 12, characterized in that a handle is attached on the proximal end of said connecting rod.

14. Instrument according to claim 12, characterized in that a manipulator is disposed on said first shaft.

15. Instrument according to claim 12, characterized in that an optical endoscopic system is axially inserted into said first shaft.

16. Instrument according to claim 15, characterized in that said optical endoscopic system is a retro-type optical system and projects beyond a distal end of said first shaft.

17. Instrument according to claim 15, characterized in that said optical endoscopic system is adapted to be axially positioned.

18. Instrument according to claim 17, characterized in that said optical endoscopic system is inserted into a second shaft and is adapted to be positioned jointly with said second shaft.

19. Instrument according to claim 18, characterized in that a manipulator such as a thumb ring is mounted on said second shaft.

20. Instrument according to claim 1, characterized in that said HF electrode array is comprised of a monopolar electrode.

21. Instrument according to claim 1, characterized by HF electrodes cutting having one electrode formed by the electrode and one electrode constituted by said outside surface.

22. Instrument according to claim 1, characterized in that the coil shape is substantially the same contour as the contour of the outside surface.

23. Instrument according to claim 1, characterized in that said coil is moved in a direction towards a proximal end of the instrument body for severing tissue.

* * * * *